United States Patent [19]
Erikson

[11] 3,938,501
[45] Feb. 17, 1976

[54] CATHETER FOR RADIOLOGICAL RENAL AORTOGRAPHY AND SELECTIVE ARTERIOGRAPHY

[75] Inventor: Uno Eugen Erikson, Uppsala, Sweden

[73] Assignee: Siemens Aktiengesellschaft, Germany

[22] Filed: Nov. 1, 1973

[21] Appl. No.: 411,815

[30] Foreign Application Priority Data
Nov. 3, 1972  Sweden ............................... 253/72

[52] U.S. Cl. ............................... 128/2 A; 128/348
[51] Int. Cl.² ............................................ A61B 6/02
[58] Field of Search ........... 128/2 A, 2 R, 348, 349, 128/350, 351, 239, 276

[56] References Cited
UNITED STATES PATENTS
3,612,038  10/1971  Halligan ........................ 128/348 X
FOREIGN PATENTS OR APPLICATIONS
1,027,322  2/1953  France .................. 128/348

OTHER PUBLICATIONS
"Bourassa" Cardiovascular Catheters, U.S.C.I. Brochure, June 1972.
A.C.M.I. Catalogue, 1952, RC901-5A5, p. 182.
Catheters For Cardiology, U.S.C.I. Catalogue, 1963, p. 10.
A.C.M.I. Catalogue, 1960, RC901.5A5, p. 24.

*Primary Examiner*—Kyle L. Howell
*Attorney, Agent, or Firm*—Haseltine, Lake & Waters

[57] ABSTRACT

A catheter for the injection of liquid X-ray contrast media into the vascular systems of a patient, which is characterized in that the end of the catheter proximate its introduction into the patient terminates in a point and is bent at an angle near this point, and includes an outwardly directed aperture in the central region of the bend. The catheter facilitates renal aortography and selective arteriography to be simultaneously effected without the need of interchanging the catheter.

5 Claims, 2 Drawing Figures

CATHETER FOR RADIOLOGICAL RENAL AORTOGRAPHY AND SELECTIVE ARTERIOGRAPHY

FIELD OF THE INVENTION

The present invention relates to a catheter utilized for the injection of liquid X-ray contrast media into the vascular system of a patient for the implementation of renal aortography and selective arteriography.

The angiographic examination of the kidneys has presently become a basic routine in conjunction with the studies of patients who are, for example, affected by hypertension. In the case of hypertension, the examination primarily concerns itself with the main and lateral branches of the renal arteries.

DISCUSSION OF THE PRIOR ART

The customary method of exploration comprises the employment of different projections in renal aortography with the patient lying stretched out in order to provide visualization of the branches of the renal arteries. To this effect, radio-opaque media are introduced into the aorta through the intermediary of a straight catheter. When the patient exhibits pathological findings, the examination is supplemented by selective arteriography i.e. studies covering the pathological area. Only one artery can be examined at any time by the use of several projections. This method is not only time-consuming and troublesome for the patient but also exposes him to an increased hazard which are caused by the risk of complications.

SUMMARY OF THE INVENTION

Accordingly, the present invention provides for a catheter for the injection of liquid X-ray contrast media into the vascular systems of a patient, which is characterized in that the end of the catheter proximate its introduction into the patient terminates in a point and is bent at an angle near this point, and includes an outwardly directed aperture in the central section of the bend.

It is, accordingly, an object of the present invention to provide a catheter facilitating renal aortography and selective arteriography to be simultaneously effected without the need of interchanging the catheter. Another object of this invention is to provide a novel catheter permitting a reduction in the number of projections required for the complete examination of a patient.

BRIEF DESCRIPTION OF THE DRAWING

These and other objects and advantages of the invention will be better understood from the following detailed description, taken in conjunction with accompanying drawing, in which.

DETAILED DESCRIPTION

Figure 1:
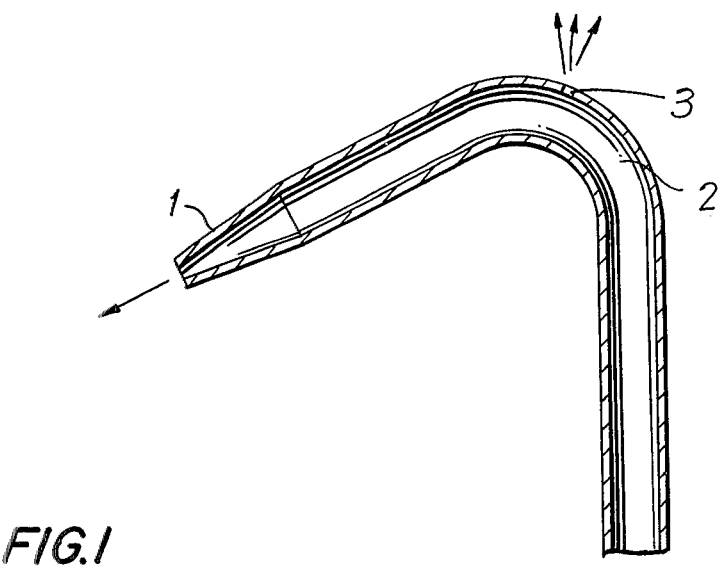
FIG. 1 shows a sectional view of a portion of a catheter constructed in accordance with the present invention.
Figure 2:
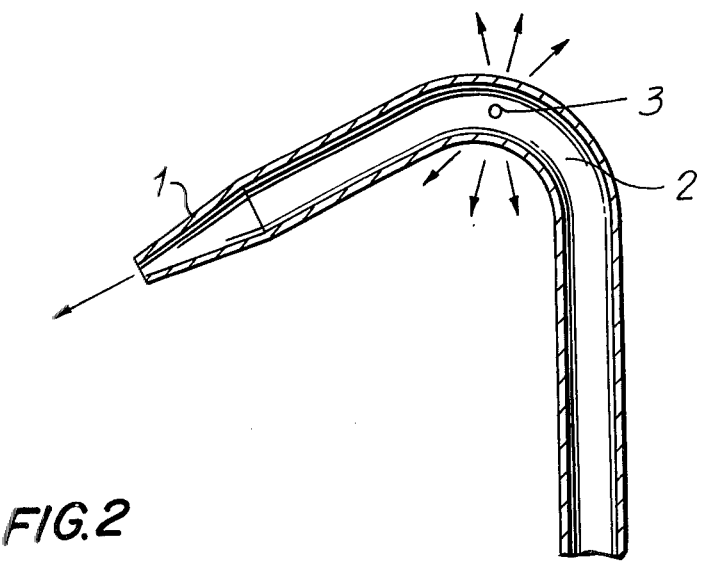
FIG. 2 illustrates a sectional view of a portion of a second embodiment of a catheter constructed in accordance with the invention.

Referring now to the accompanying drawing which illustrates in FIGS. 1 and 2 embodiments of the catheter, the latter comprises a generally flexible tubular member which terminates, at the end thereof proximate the introduction into a patient, in an open point 1, and forming a taper for a short distance. The catheter is bent near that end at an angle of about 80° so as to preferably correspond to the angle between the artery of the body and the renal artery. Within the central section the bent portion or length 2 the wall of the catheter includes an outwardly directed aperture 3, the aperture extending radially outwardly in the embodiment of FIG. 1, and laterally or sideways in the embodiment of FIG. 2.

The diameters and lengths of the catheters illustrated coincide with the customary dimensions of normal catheters. The diameters of the apertures are so dimensioned with respect to each other whereby about 15% of any radiopaque medium conveyed through the catheter flows through aperture 3 and roughly 85% through the opening in point 1. In a catheter having a diameter of 1.8 mm, the diameter of aperture 3 may be 1 mm while the opening in point 1 may have, for example, a diameter of 1.5 mm.

The aperture 3 is generally located at a distance of approximately 10 to 18mm from the outlet opening of the catheter within the central region of the bent catheter portion 2.

An application of the catheter according to the present invention is illustrated in the following example:

A catheter of about 80 cm in length is introduced into a patient according to the Seldinger technique. The catheter is introduced so that point 1 comes to rest on a level par with the orifice of the renal arteries of the kidney to be examined. About 30 ml radiopaque medium is then injected through the catheter under a pressure of 5 kp/cm$^2$. In this manner information about the number of the renal arteries and any possible anomalies of their branches may be readily obtained. Subsequently, selective catheterizations are carried out with the same catheter by injecting 10 ml radiopaque medium at a pressure of 3 kp/cm$^2$. In this connection, the renal artery to be catheterized, and concurrently a short segment of the aorta, as well as the renal artery on the opposite side of the aorta, are filled with contrast medium through the aperture 3. Two projections of the arteries are obtained in this manner by catheterization of the renal arteries, and by turning the patient through about 15° so that the kidney which is to be catheterized is simultaneously rotated through about 15° and thus displaced upwardly. These projections are obtained without producing any adverse effect on the intestinal arteries resulting, for instance, from an undesirable injection of contrast medium.

While there has been shown what is considered to be the preferred embodiment of the invention, it will be obvious that modifications may be made which come within the scope of the disclosure of the specification.

What is claimed is:

1. Catheter for the injection of liquid X-ray contrast media into the vascular system of a patient for the implementation of renal aortography and selective arteriography comprising a flexible tubular catheter member, one end of said catheter member terminating into a tapered point having an opening communicating with the interior of the catheter and adapted to be introduced into the patient, said catheter member being bent through a predetermined angle in proximity to said point end so as to form a first short linear portion between said tapered point and the bend and a second lengthier linear tubular portion, said first and second linear tubular portions subtending an acute angle therebetween, and through aperture means being formed in said catheter member in the central region of its bend intermediate said first and second linear tubular portions, said aperture means being dimensioned to facilitate flow therethrough of approximately one-seventh the quantity of the contrast media flowing through said catheter, and said first short linear portion being of a length so as to provide a predetermined distance between said opening at the tapered point and said aperture means whereby said catheter is adapted to be positioned in the renal artery of the patient for concurrently effecting renal aortography and selective arteriography.

2. Catheter as claimed in claim 1, said catheter being bent so as to subtend an angle between the bent catheter member portions of about 80°.

3. Catheter as claimed in claim 1, said aperture means in said bent catheter member region being spaced from the pointed end of said catheter a distance of 10 to 18 mm.

4. Catheter as claimed in claim 1, said bent catheter member portion being arcuately curved, and said aperture means being radially outwardly directed at the central region of said curved portion.

5. Catheter as claimed in claim 1, said aperture means extending laterally with respect to the bending plane of said catheter member.

* * * * *